United States Patent
Singh et al.

(10) Patent No.: US 10,493,558 B2
(45) Date of Patent: Dec. 3, 2019

(54) NANOPROCESSING AND HETEROSTRUCTURING OF SILK

(71) Applicant: INDIAN INSTITUTE OF SCIENCE EDUCATION AND RESEARCH, Punjab (IN)

(72) Inventors: Kamal Priya Singh, Punjab (IN); Mehra Singh Sidhu, Punjab (IN); Bhupesh Kumar, Punjab (IN)

(73) Assignee: INDIAN INSTITUTE OF SCIENCE EDUCATION AND RESEARCH, Punjab (IN)

( * ) Notice: Subject to any disclaimer, the term of this patent is extended or adjusted under 35 U.S.C. 154(b) by 0 days.

(21) Appl. No.: 16/103,751

(22) Filed: Aug. 14, 2018

(65) Prior Publication Data
US 2018/0354066 A1 Dec. 13, 2018

Related U.S. Application Data

(63) Continuation-in-part of application No. PCT/IB2017/051252, filed on Mar. 3, 2017.

(30) Foreign Application Priority Data

Mar. 6, 2016 (IN) .............................. 201611000500

(51) Int. Cl.
*B23K 26/00* (2014.01)
*B81C 1/00* (2006.01)
(Continued)

(52) U.S. Cl.
CPC ........ *B23K 26/0006* (2013.01); *A61L 27/227* (2013.01); *B23K 26/032* (2013.01);
(Continued)

(58) Field of Classification Search
CPC ............ B23K 26/0006; B23K 26/0624; B23K 26/32; B23K 26/046; B23K 26/0626;
(Continued)

(56) References Cited

U.S. PATENT DOCUMENTS

2014/0205797 A1 7/2014 Kaplan et al.

FOREIGN PATENT DOCUMENTS

CN 102974936 B 4/2015

OTHER PUBLICATIONS

Communication (International Search Report and Written Opinion) issued by the International Searching Authority in Patent Application No. PCT/IB2017/051252 dated Jun. 29, 2017, 11 pages total.
(Continued)

*Primary Examiner* — Nicole M Ippolito
*Assistant Examiner* — Hanway Chang
(74) *Attorney, Agent, or Firm* — Troutman Sanders LLP

(57) ABSTRACT

The present invention relates to nanoprocessing and heterostructuring of silk. It has been shown that few-cycle femtosecond pulses are ideal for controlled nanoprocessing and heterostructuring of silk in air. Two qualitatively different responses, ablation and bulging, were observed for high and low laser fluence, respectively. Using this approach, new classes of silk-based functional topological microstructures and heterostructures which can be optically propelled in air as well as on fluids remotely with good control have been fabricated.

20 Claims, 11 Drawing Sheets
(11 of 11 Drawing Sheet(s) Filed in Color)

(51) Int. Cl.
| | |
|---|---|
| B23K 26/0622 | (2014.01) |
| A61L 27/22 | (2006.01) |
| B23K 26/03 | (2006.01) |
| B23K 26/046 | (2014.01) |
| B23K 26/06 | (2014.01) |
| B23K 26/22 | (2006.01) |
| B29C 65/16 | (2006.01) |
| B29C 65/00 | (2006.01) |
| G01Q 40/00 | (2010.01) |
| G01Q 70/16 | (2010.01) |
| B29K 33/00 | (2006.01) |
| B29K 83/00 | (2006.01) |
| B29L 11/00 | (2006.01) |
| B29L 31/40 | (2006.01) |

(52) U.S. Cl.
CPC ........ *B23K 26/046* (2013.01); *B23K 26/0624* (2015.10); *B23K 26/0626* (2013.01); *B23K 26/22* (2013.01); *B29C 65/1616* (2013.01); *B29C 66/0224* (2013.01); *B29C 66/0324* (2013.01); *B29C 66/69* (2013.01); *B29C 66/712* (2013.01); *B29C 66/729* (2013.01); *B81C 1/00126* (2013.01); *G01Q 40/00* (2013.01); *G01Q 70/16* (2013.01); *B29K 2033/12* (2013.01); *B29K 2083/00* (2013.01); *B29K 2089/00* (2013.01); *B29L 2011/0041* (2013.01); *B29L 2031/40* (2013.01); *B81C 2201/038* (2013.01)

(58) Field of Classification Search
CPC ................ B23K 26/22; B29C 65/1616; B29C 66/0224; B29C 66/0324; B29C 66/69; B29C 66/712; B29C 66/729; B81C 1/00126; B81C 2201/038; B29K 2033/12; B29K 2083/00; B29K 2089/00; B29L 2011/0041; B29L 2031/40; A61L 27/227; G01Q 40/00; G01Q 70/16
USPC ........................ 850/19, 20; 250/492.1, 491.1
See application file for complete search history.

(56) References Cited

OTHER PUBLICATIONS

Lazare, S. et al., "Bombyx Mori Silk Protein Films Microprocessing with a Nanosecond Ultraviolet Laser and a Femtosecond Laser Workstation: Theory and Experiments" Applied Physics A: Materials Science & Processing (2012) vol. 106, No. 1, pp. 67-77.
Communication (International Preliminary Report on Patentability) issued by the International Searching Authority in Patent Application No. PCT/IB2017/051252 dated Sep. 11, 2018, 8 pages total.

NANOPROCESSING AND HETEROSTRUCTURING OF SILK

CROSS-REFERENCE TO RELATED APPLICATIONS

This application is a continuation-in-part of International Patent Application No. PCT/IB2017/051252, filed on Mar. 3, 2017, which published as WO 2017/153876 A1 on Sep. 14, 2017, and claims priority of IN201611000500, filed Mar. 6, 2016, the disclosures of each of which are hereby incorporated by reference in their entirety.

FIELD OF THE INVENTION

The present invention is in the field of nanotechnology and particularly relates to the nanoprocessing and heterostructuring of natural fibers like silk etc. The present invention involves ultrafast laser based modification and seamless micro-welding of natural fibers including spider silks.

BACKGROUND

Spider silk is an ancient biomaterial that is tougher than steel, yet elastic and light weight. The superior physical properties of spider silk make it an attractive biocompatible functional material. Various applications of silk in water collection, biomedical devices and optics have been demonstrated. Silk fibers with enhanced toughness and possessing electrical and magnetic properties have been created by infiltrating them with various (non-) metallic nanoparticles. A great deal of experimental and theoretical efforts has been made to understand relation between structure and its functional properties. However, to realize true potential of silk for diverse nanoengineering, technological and other applications two fundamental difficulties exist. First, it is difficult to manipulate the silk with nanoscale precision due to high toughness and finesse. One needs to devise a noninvasive nano-processing approach for silk while preserving its key structural building blocks and also retaining its excellent physical properties. Second, it is not yet fully explored, how to integrate silk with other modern materials such as metals, dielectrics, synthetic polymers thereby combining their best properties. Thus, it is vital to devise a new approach to remove these two bottlenecks.

Previously, chemical processing techniques have been proposed to make silk films and bulk structures for various applications. Ablation of spider dragline by nanosecond (ns) pulses of deep ultraviolet (VUV) radiation has also been studied. Moore et al., in 2006 made a first attempt to process the dragline silk of black widow spider (*Latrodectus hesperus*) using nanosecond UV laser ($\lambda$=157 nm) under vacuum controlled conditions. Besides requiring high vacuum conditions, the VUV light degraded the silk structure leading to loss of function and strength. Thus, it is apparent that it is difficult to nano-machine silk fibers in controlled conditions. Moreover, it is difficult to micro-weld silk fibers such as spider silk with themselves or other materials.

Recent advent of amplified ultrafast lasers has drawn considerable interest for material processing. These lasers could provide higher precision and less thermal damage than conventional lasers with rather long pulse durations of several tens of nanoseconds. Ultrafast lasers are very efficient for direct micromachining of materials because of their non-contact nature, which allows micro-processing and surface patterning of materials with minimized mechanical and thermal deformations by rapid pulse energy deposition.

Since last decades, short femtosecond (fs) pulses have evolved into a preferred tool over picosecond (ps) and nanosecond (ns) pulses in precise material processing with low collateral damage. Femtosecond (fs) lasers have made a mark to be used in corneal refractive surgery and many more surgical procedures. The effects of different fs-laser parameters such as pulse energy, wavelength, pulse width, and tissue depth on the operation performance have been widely investigated. But, fs-lasers processing technology has not been used yet to fuse/weld threads/fibers/sutures that holds the donor tissues in place during healing. Fs-lasers could be proposed as a future surgical tool for seamless micro-welding for joining biological tissues including cornea. Therefore, it is a vital need to establish an optical approach to modify threads/fibers/sutures and micro-weld on surfaces using such lasers.

The present invention is an attempt to overcome problems in the prior art and for the first time shows that the interaction of spider silk with few-cycle fs pulses generated by fs lasers offers a unique opportunity for its controlled nanoprocessing and heterostructuring with diverse materials in air. Precisely, in order to overcome limitations in the prior art, the inventors have developed femtosecond laser based framework to modify and weld (seamlessly) the thin silk fibers with a high precision. This is a significant step to realize spider silk fibers and other natural fibers in utilization as threads/sutures for fabricating nano-devices, allografting, designing pressure, force and vibration sensors.

OBJECTIVES OF THE PRESENT INVENTION

The main objective of the present invention is to provide a novel approach for nanoprocessing of silk in air, including spider silk by application of few-cycle fs pulses.

Yet another objective of the present invention is to modify optical as well as physico-chemical properties of natural spider silk fibers and seamless welding of such ultrathin fibers using super high speed lasers.

Yet another objective of the present invention is to provide non-invasive localized nanoshaping of silk while retaining its key molecular structure.

Yet another objective of the present invention is to provide an optical approach (using fs pulses) to fabricate diverse topological microstructures.

Yet another objective of the present invention is to provide robust heterostructuring of silk with Cu, glass, Kevlar, Polyvinyl carbonate(PVC), Poly (methyl methacrylate) (PMMA) and Poly-di-methyl-siloxane (PDMS) by its seamless micro-welding.

Yet another objective of the present invention is to provide an apparatus for microstructuring and heterostructuring of silk, which comprises of a laser light source generating a femtosecond laser beam so that the same can be applied for modification and seamless welding of silk fibers.

SUMMARY OF THE INVENTION

The present invention offers a novel approach for nanoprocessing and heterostructuring of silk by application of few-cycle fs pulses. An optical approach for modifying optical, physico-chemical properties of natural spider silk fibers and for seamless welding of such ultrathin fibers with artificial and biological materials using a super high speed laser has been presented. The technique of the present invention quantified the silk response, i.e., initially bulging and later ablating as a function of applied laser fluence. These regimes were exploited for non-invasive localized nanoshaping (nanocut, grooves, rods, nanotip) while retaining its key molecular structure.

The present invention successfully utilizes the bulging regime for seamless microwelding of two independent silk fibers. So far, there is no known route to merge two silk fibers in air, after they have been spun by the spider. This is essential to develop capability to fabricate all-silk based designer structures. The present invention demonstrates merging of the contact region of two different silk fibers, when these were exposed to fs pulses for 10-60 s. The optical microscopy, confocal microscopy, and SEM images of welded region confirmed that welded regions had no cracks and weld-joints retained good surface smoothness. To demonstrate robustness and repeatability of techniques we welded silk fibers of various diameters in different configurations. Most remarkably, robust heterostructuring of silk with Cu, glass, Kevlar, Polyvinyl carbonate (PVC), Poly (methyl methacrylate) (PMMA) and Poly-di-methyl-siloxane (PDMS) by its seamless micro-welding was demonstrated. The optical approach allowed the inventors to fabricate diverse topological microstructures, such as the Möbius strip, chiral helices, and knots which were shown to be propelled by light in air or on water with good control.

Moreover, analysis of Raman bands of micro-welded joints reveal that the polypeptide backbone remains intact while perturbing its weak hydrogen bonds. The approach was used for fabricating a new class of silk based functional topological microstructures, such as Mobius strip, chiral helices, and cantilever or trampoline-like sensors, which were optically propelled in air as well as on fluids remotely with good control. The sensors in the present application can be nano-sensors.

In some aspects, the present disclosure relates to a non-invasive method for nanoprocessing of silk comprising: quantifying optical non-linear multiphoton response of a silk material as a function of laser fluence induced by a pulsed femtosecond laser beam of predetermined laser characteristics; and microstructuring or heterostructuring of silk material upon exposure of the femtosecond laser beam.

In some embodiments, quantifying the non-linear multiphoton response of a silk material comprises: focusing the femtosecond laser beam at a focal point under ambient conditions; exposing a portion of the silk material at the focal point; raster scanning the portion of the silk material in the focus; displaying real time image of the exposed portion of the silk material; and determining change in physical dimension of the portion of the silk material by varying the laser fluence at the portion of the silk material.

In some embodiments, determining a change in the physical dimension of the portion of silk material by varying the laser fluence comprises: determining an effect of a bulging at the portion of the silk material for a laser fluence range between 1.25 to 3.0 mJ/μm2; and determining an effect of a plasma ablation at the portion of the silk material for a laser fluence range between 3.0 mJ/um$^2$ to 9 mJ/μm$^2$, wherein the bulging and the plasma ablation defines a change in the physical dimension of the silk material without causing any collateral damage onto the material, the effects of bulging and plasma ablation being based on non-linear multiphoton absorption response of the pulsed femtosecond laser beam towards the silk material.

In some embodiments, exposing the portion of silk material at the focal point comprises: focusing the femto-second (fs) laser pulses through a chirp mirror based dispersion compensated triplet lens objective; aligning the silk sample in the laser focus by imaging through a dichroic mirror; aligning the silk sample in the laser focus by diffraction imaging in transmission.

In some embodiments, the step of exposing comprises: exposing the portion of the silk material by varying an exposure time within a range of 10 ms to 100 s; wherein the step of raster scanning comprises periodically scanning the portion of the silk material at a scan rate of 2 mm/s; and wherein the step of varying the laser fluence comprises varying the laser fluence within a range of 0.25 to 9.0 mJ/μm$^2$.

In another aspect, the present disclosure provides a system for quantifying an optical response of a silk material, the system comprising: a focusing unit for focusing a pulsed femtosecond laser beam of predetermined laser characteristics at a focal point; a three dimensionally movable translation stage support of holding the silk material for exposing a portion of the silk material at the focal point; displaying unit for displaying real time image of focused portion of the silk material and thereby determining change in physical dimension of the portion of the silk material by varying the laser fluence at the portion of the silk material.

In some embodiments, the focusing unit comprises dispersion compensated mirrors, a dielectric broadband dichroic mirror, a triplet lens objective, a high speed mechanical shutter and/or a neutral density filter.

In some embodiments, the displaying unit comprises two high resolution charged couple devices (CCDs) for diffraction imaging and in line focusing for real time monitoring.

In some embodiments, determining a change(s) in a physical dimension of the portion of a silk material by varying the laser fluence comprises: determining an effect of a bulging at the portion of the silk material for a laser fluence range between 1.25 to 3.0 mJ/μm2; and determining an effect of a plasma ablation at the portion of the silk material for a laser fluence range between 3.0 mJ/um2 to 9 mJ/μm2, wherein the bulging and the plasma ablation defines a change in physical dimension of the silk material without causing any collateral damage onto the material, the effects of bulging and plasma ablation are determined by exploiting the non-linear multiphoton absorption response of the pulsed femtosecond laser beam towards the silk material.

In another aspect, the present disclosure provides a method for the preparation of a silk based nanosensor comprising: cleaning a substrate base using ultrasonication; placing the silk thread over the substrate and microwelding one or more silk threads onto the substrate, wherein silk threads comprise the nanostructured or heterostructured silk fibers; and wherein nano structuring or heterostructuring involves the steps of (i.) quantifying non-linear multiphoton response of a silk material as a function of laser fluence induced by a pulsed femtosecond laser beam of predetermined laser characteristics; and (ii.) micro structuring or heterostructuring of silk material upon exposure of the femtosecond laser beam; and obtaining the fabricated biosensor and propelling the same in air or a fluid.

In some embodiments, the method for the preparation of a cantilever nanosensor comprises: cleaning the substrate using a methanol:acetone solution and ultra-sonicating for a suitable time period; extracting and braiding two threads of spider silk dragline; fusing or welding the end of threads fs-pulses; exposing the threads to the pulses; welding one end of the thread with substrate; bending the other fused end at a certain angle as a function of exposure time and energy; and obtaining the silk cantilever nanosensor.

In some embodiments, the method for the preparation of a cantilever nanosensor comprises: cleaning the substrate using 3:1 (methanol:acetone) solution and ultra-sonicating for 30 min; extracting and braiding two threads of spider silk dragline of 1-3 µm; fusing or welding the end of threads with nanojoule fs-pulses; exposing the threads to the pulses 100 times at the speed of 2 mm/s with the pulsed average energy between 0.8-1 nJ; welding one end of the thread with substrate with an exposure time of about 30 s and energy between 0.8-1.0 nJ; bending the other fused end at an angle between 45-60° as a function of exposure time (0.3-5 s) and energy between 0.8-1.0 nJ; and obtaining the silk cantilever nanosensor.

In some embodiments, the method for the preparation of a trampoline nanosensor comprises: fabricating the substrate by cutting a PVC sheet by automated scan of femtosecond laser pulses with certain incident energy and a repetition rate, followed by sifting; cleaning the substrate using ultra-sonication for suitable time at room temperature; placing the substrate on a glass slide and then placing the spider silk fibers over in a criss-cross manner; exposing the four corners of the fabricated substrate with Fs-laser pulses for micro-welding of silk on PVC substrate; placing a mirror at the center of criss-crossed silk threads and microwelding it with aforementioned parameters; and obtaining the fabricated trampoline sensor.

In some embodiments, the method for the preparation of a trampoline nanosensor comprises: fabricating the substrate by cutting a PVC sheet of about 150 µm thickness (outer parameters of about 4×4 mm2a and inner square area of about 3×3 mm2) by automated scan of femtosecond laser pulses with an incident energy of about 50 µJ and a repetition rate of 50 repetitions with a scan rate of 2 mm/s. Z-axis (focal plane), sifting with a step of 30 µm per repetition; cleaning the substrate using ultrasonication for about 20 min at room temperature; placing the substrate on a glass slide and then placing the spider silk fibers over in a criss-cross manner; exposing the four corners of the fabricated substrate with Fs-laser pulses for micro-welding of silk on PVC substrate with following parameters: Laser energy: 0.8-1 nJ, exposure time between 30-60 s at the scan rate of 2 mm/s; placing a mirror at the center of criss-crossed silk threads and microwelding it with aforementioned parameters; and obtaining the fabricated trampoline sensor. In some embodiments, the substrate(s) used for micro-welding of silk may be selected from, but are not limited to, copper, glass, kevlar and polyvinylcarbonate (PVC) sheet.

In another aspect, the present disclosure provides a cantilever nanosensor created by any of the methods disclosed herein.

In another aspect, the present disclosure provides a trampoline nanosensor created by any of the methods disclosed herein.

In another aspect, the present disclosure provides a method for testing the sensitivity of a nanosensor (e.g., a cantilever or trampoline nanosensor) by propelling the nanosensor in air or a fluid medium and checking its responsiveness to pressure, force, light or any other external factor.

In some embodiments of the disclosed methods, micro structuring comprises the preparation of topological micro-structures including, but not limited to, micro-springs, coiled solenoid, mobius strips, chiral helices, or knots.

In some embodiments of the disclosed methods, hetero-structuring comprises seamless welding of the silk material with an artificial or biological material.

In some embodiments, seamless welding of silk material comprises: contacting the silk material with the artificial or biological material; and focusing the femtosecond laser beam to the site of contact resulting in fabrication of a micro welded structure by operating the laser beam at bulging regime.

In some embodiments of the disclosed methods, the ambient conditions for performing the methods disclosed herein include a temperature between 24°-26° C. in air and a relative humidity between 45% to 55%.

In some embodiments of the disclosed methods, the predetermined laser characteristics comprise a pulse width of 7-10 fs, a wavelength of 800 nm, a pulse energy of 2 nJ, and a repetition rate of 85 MHz.

In some embodiments of the disclosed methods, the femtosecond laser beam used for micro-welding has an energy between 0.8-1.0 nJ and an exposure time between 30-60 s having a scan rate of 2 mm/s.

In some embodiments of the disclosed methods, systems, and/or sensors, the silk material is spider silk fiber. In certain embodiments, the silk material has a 0.8 to 6 µm physical diameter.

In some embodiments of the disclosed methods, systems, and/or sensors, the biological material includes, but is not limited to, silk or a biological tissue.

In some embodiments of the disclosed methods, systems, and/or sensors, the artificial material includes, but is not limited to, copper, glass, Kevlar, Polyvinyl carbonate (PVC), Poly (methyl methacrylate) (PMMA) and Poly-di-methyl-siloxane (PDMS).

These and other aspects of the present invention will be apparent to those of ordinary skill in the art in the following description, drawings and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
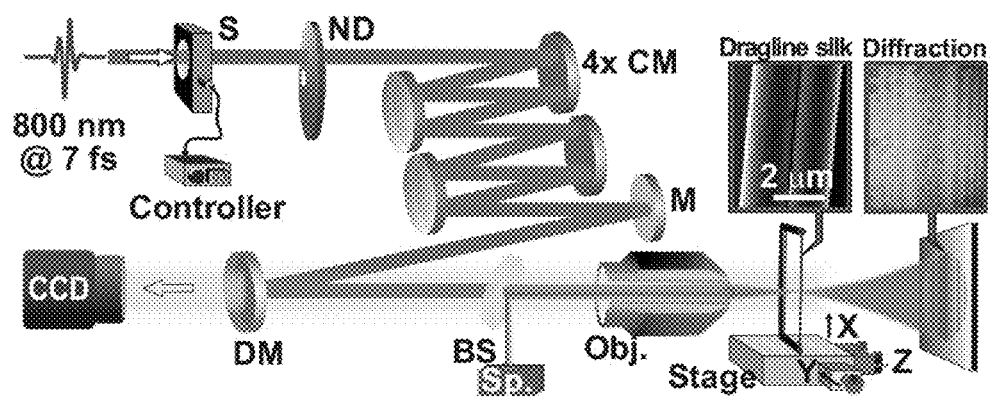
FIG. 1. Schematics of the experimental set up. The fs pulses (7-10 fs, 800 nm, 2.2 nJ at 85 MHz rep. rate) were focused on to 5 µm spot diameter through a chirp-mirror based dispersion compensated objective. Silk sample was mounted on a computer controlled 3-axis nano-positioner stage. Insets: SEM image of silk sample, and its typical optical diffraction pattern. S: shutter, ND: neutral density filter, DM: Dielectric broadband dichroic mirror, CM: chirp mirror, M: Ag-mirror, Obj: objective, Stage: Automated X-Y-Z translation stage, CCD: two high resolution charged couple devices (CCD), sp: spectrophotometer.

While the invention is susceptible to various modifications and alternative forms, specific embodiment thereof has been shown by way of example and will be described in detail below. It should be understood, however that it is not intended to limit the invention to the particular forms disclosed, but on the contrary, the invention is to cover all modifications, equivalents, and alternatives falling within the spirit and the scope of the invention.

Accordingly, the present invention provides a novel approach for nanoprocessing and heterostructuring of silk by application of few-cycle fs pulses. The process of the present invention involves non-invasive localized nanoshaping of silk while retaining its key molecular structure. Importantly, the optical approach (using fs pulses) of the present invention is utilizable to fabricate diverse topological microstructures, such as the Möbius strip, chiral helices, and knots which were shown to be propelled by light in air or on water with good control. Robust heterostructuring of silk with Cu, glass, Kevlar, Polyvinyl carbonate (PVC), Poly (methyl methacrylate) (PMMA) and Poly-di-methyl-siloxane (PDMS) by its seamless micro-welding has been achieved.

Accordingly, a system according to the present invention for modification and seamless welding of fibers comprises: a fs-laser light source; a neutral density attenuator controlling the power of the fs-laser beam; a fixing unit (rectangle frame) to hold the spider silk sample in air; a dispersion compensated chirped mirror based optical setup for optimal pulse width (7-10 fs) to process spider silk placed on fixing unit; and a focus control part controlling the focus of the focused laser beam.

The approach of the present invention involved exploitation of the non-linear multiphoton absorption response of fs-pulse towards silk material to bulge or ablate the silk material.

Theoretically, the multiphoton absorption is determined by the following equation, $$\frac{dI}{dz} = \alpha_1 I + \alpha_2 I^2 + \alpha_3 I^3 + \alpha_4 I^4 + \alpha_5 I^5 \quad (1)$$

where, I is the intensity of incident light beam propagating along the z-axis. The coefficients $\alpha_1$, $\alpha_2$, $\alpha_3$, $\alpha_4$, $\alpha_5$ are one-, two-, three-, four- and five-photon absorption coefficients for a given medium, respectively. For silk fiber of diameter $D_0$, we define absorption, $A=(dI/I)(1/D_0)$, which, using Eq. (1) becomes a polynomial of third-order, $A=\alpha_1+\alpha_2 I+\alpha_3 I^2+\alpha_4 I^3+\alpha_4 I^4+\alpha_5 I^5$. This mixed fit was used to fit the experimental data. A comparison of mixed fit with cases of pure 2-, 3-, 4-, and 5-photon absorption processes are also shown for comparison. The values of coefficients are, $\alpha_2=1\times10^{-2}$ cm/GW, $\alpha_3=2\times10^{-5}$ cm$^3$/GW$^2$, $\alpha_4=4\times10^{-6}$ cm$^5$/GW$^3$, $\alpha_5=5\times10^{-7}$ cm$^7$/GW$^4$. Our fit analysis suggests that as the intensity of the pulses increases, the absorption is dominated by progressively higher order multiphoton processes.

Bulging of silk material allows it to mould/weld with different artificial or biological materials. Precise ablations using fs-pulses allows to cut the silk material limited to focal volume. Optical microscopy and SEM imaging of the moulded/welded region was done to visualize and monitor the changes.

The ablation regime allowed diverse non-invasive machining capability of the silk fibers with nanometer precision. Silk was diced into micro-rods reproducibly. The ends of the micro-rods showed fine cuts as well as good surface quality. The high precision processing and absence of collateral damage allowed the inventors to fabricate the fine silk-nanotip within nano range. The nano-tips, cuts and grooves remained stable in air as well as in vacuum akin to the pristine silk. In order to prove that the fs pulse ablation did not alter the native molecular structure of the silk significantly, the inventors obtained its Raman spectra in the close vicinity of ablated region. It was observed that in spite of the ablation, most of the prominent Raman bands remain preserved. The preservation of the prominent Raman bands after the ablation offers an unparalleled advantage of short fs pulses in non-destructive nanoshaping of silk in air.

The bulging regime, however, offers a qualitatively different and new set of nanoprocessing capabilities. As per the existing literature, no route is known to permanently microbend the silk because of its high-elasticity and toughness. The inventors exploited the bulging response to demonstrate the confined bending of fibers at any angle. The bent fibers retained good surface smoothness and remained stable in air and vacuum conditions. The inventors successfully utilized the bulging regime for seamless microwelding of two independent silk fibers. So far, there is no known route to merge two silk fibers, after they have been spun by the spider. This is essential to develop capability to fabricate all-silk based designer structures. The inventors demonstrated merging of the contact region of two different silk fibers, when these were exposed to fs pulses. Both the optical microscopy and SEM images confirmed a seamless fusion/welding of the two fibers while retaining the surface smoothness of welded region. Many silk fibers of different diameters were microwelded in different configurations that demonstrated robustness and reproducibility of the technique.

Remarkably, the bulging regime facilitates the fabrication of precise heterostructures of spider silk by microwelding it with materials like Cu, glass, Kevlar, Polyvinyl carbonate (PVC), Poly (methyl methacrylate) (PMMA) and Poly-dimethyl-siloxane (PDMS). The employed fs pulses also avoid any collateral damage to the silk as well as the substrate material. Moreover, this preserved the key building blocks of silk that allows to potentially combine their best properties. To achieve fine microwelding, the silk fiber was placed in contact with other materials and exposed to the fs pulses. These composite structures remained stable both in air as well as in high vacuum. The ultimate tensile strength of diverse micro-welded joints was measured and was found to be comparable to the strength of the pristine silk fiber from the same spider. The micro-Raman analysis was used to understand the molecular scale deformation in silk for all microwelded joints. It was further compared with the spectra of the native silk. The Raman spectra of the welded silk joint were similar to the native one. This suggests that the polypeptide backbone (C—C, C—H, C=O etc) was also intact during microwelding. However, the Raman bands were broader, which was probably due to higher heterogeneity and dis-orientation of the side-chains. The reconfigurable nature of the polypeptide chains in silk perhaps make Vander waal or hydrogen bonds with substrate, leading to an atomic scale affinity between silk and diverse materials. Meanwhile, the key molecular bonds of the silk remain preserved that corroborated well with the observed breaking strength of microwelded joints.

In one embodiment of the invention, a non-invasive method for nanoprocessing of silk has been provided. The method comprising quantifying optical response of a silk material as a function of laser fluence induced by femtosecond laser pulses; and microstructuring or heterostructuring of silk material upon exposure of the femtosecond laser pulses.

In one embodiment, the method for micro-structuring of silk material comprises preparation of topological microstructures including but not limited to micro-springs, coiled solenoid, mobius strips, chiral helices or knots.

In another embodiment, the method for heterostructuring of silk material comprises seamless welding of the silk material with an artificial or biological material.

The method for quantifying optical response of a silk material under ambient conditions comprises: focusing a femtosecond laser beam having predetermined laser characteristics at a focal point; exposing a portion of the silk material at the focal point; raster scanning the silk sample in the focus; displaying real time image of the exposed portion of the silk material; and determining change in physical dimension of the image by changing at least one of the laser characteristics.

The proposed optical nanoprocessing framework can be exploited to fabricate silk-based functional microstructures with novel topologies. For example, by controlled twisting and welding of silk fiber, the inventors constructed a "non-orientable" Möbius strip like structure. These were made with different topological charges (1/2, 5/2; 7/2 of turns) in air and also fused with Cu or glass substrates. Chiral silk structures were also made. These were in the form of left or right-handed configuration having double or multiple strands. Moreover, by seamless welding at both ends, these helices became stable in air, glass or water surface. Other topological structures like a micro-spring, a microdroplet, a solenoid-like packing, various knotted bundles etc. were fabricated.

Due to diverse shapes, strength and elasticity in silk material, these microstructures offer various potential functionalities. For example, they can be propelled by external fields such as light with a good control. The inventors made a microscale cantilever of twisted silk bundle and welded it on a glass substrate. The free end of cantilever was a head-like structure which could be propelled in air by green-laser. Analogously, the inventors made a composite Silk-Cu microscale device that remain floated on the water surface. In a similar manner, when such structure was irradiated with cw laser, the heavier Cu-head could be propelled. These optically driven structures were durable and robust that offers a great potential for ultimate applications. It is rather possible, in principle, to articulate any shape that can be miniaturized to nanometer scale.

Thus, this study demonstrates a first optical route for controlled nanoprocessing and heterostructuring of silk by exploiting ablation and bulging regimes induced by short fs laser pulses. A wide variety of nanoshaping capabilities such as dicing, grooving, nano-tips, confined bending without causing any collateral damage. The present approach offered a comparable strength while welding of silk with modern materials including Cu, glass, Kevlar, Polyvinyl carbonate (PVC), Poly (methyl methacrylate) (PMMA) and Poly-di-methyl-siloxane (PDMS).

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Nano-processing Setup 2 nJ femtosecond-laser system (Femtolaser, Austria) having spectral range of 800 nm, Repetition rate: 85 MHz, and pulse width: 7 fs, S-high speed mechanical shutter (Thorlabs, USA), ND—Neutral density filter (Thor Labs, USA) to control incident intensity, DCM—Dispersion compensated mirrors (Femtolasers, Austria) to maintain the pulse width till focus placed at an angle of 7° to each other. Number of bounces for fs-laser beam was optimized to 4 for maintaining pulse duration of 7-10 fs at focus. DM—Dielectric broadband dichroic mirror ($\lambda$=800 nm). Lens—a triplet lens objective having thin glass lens to avoid pulse broadening with Numerical aperture 0.2, The beam spot diameter at focus was about 5 µm. Sample—Stage-Automated X-Y-Z translation stage with a precision of 1 µm, CCD—two high resolution charged couple devices (CCD) were installed, one for diffraction imaging and other in line of focusing for real time monitoring before the dichroic mirror. The white light continuum generation at focus detected using a spectrometer (Sp) justifies the non-linear multiphoton interaction fs-pulses with silk material.

Quantifying Optical Response of Silk Fiber

In order to achieve targeted delivery of fs pulses on the fine silk fiber (0.8-6 µm in diameter), it was mounted on a xyz nano-positioner stage. Coarsely, the silk fiber was aligned in the laser focus by CCD imaging through the dichroic mirror. However, for laser fluence below the damage threshold of silk, it produced a stable diffraction pattern on the screen, which was further used to carefully align the silk in focus with 100 nm precision. The pulse energy was controlled by ND filter and the exposure times (laser fluences) was varied using a mechanical shutter. The experiment was performed in the ambient conditions at Temperature 25±1° C. and 50±5% relative humidity.

The response of dragline silk was further quantified by varying the exposure time for fixed pulse energy. The silk sample (d=1-5 µm) was periodically scanned N times in the focus at 2 mm/s (exposure times 10 ms-100 s) in order to vary the laser fluence on the sample from 0.25-9.0 mJ/µm$^2$. We observed that below a threshold fluence of ~1.25 mJ/µm$^2$, for intensity below 80 GW/cm$^2$, the silk fiber remained unaffected despite the long exposure times. With increase in the laser fluence, two different regimes, namely multiphoton bulging and plasma-ablation, were observed. Bulging of silk takes place between the fluence range of 1.25-3.0 mJ/µm$^2$. The diameter of the bulging silk increased within the focal volume as a function of increment in laser fluence. In contrast, in the plasma assisted ablation was observed at 3.0 mJ/µm$^2$ or above, while with variation in the fluences, the cutting of silk fiber with sub-100 nm to micrometer range could be achieved.

Example 2

Micro-welding of Silk with Artificial Materials

Figure 6:
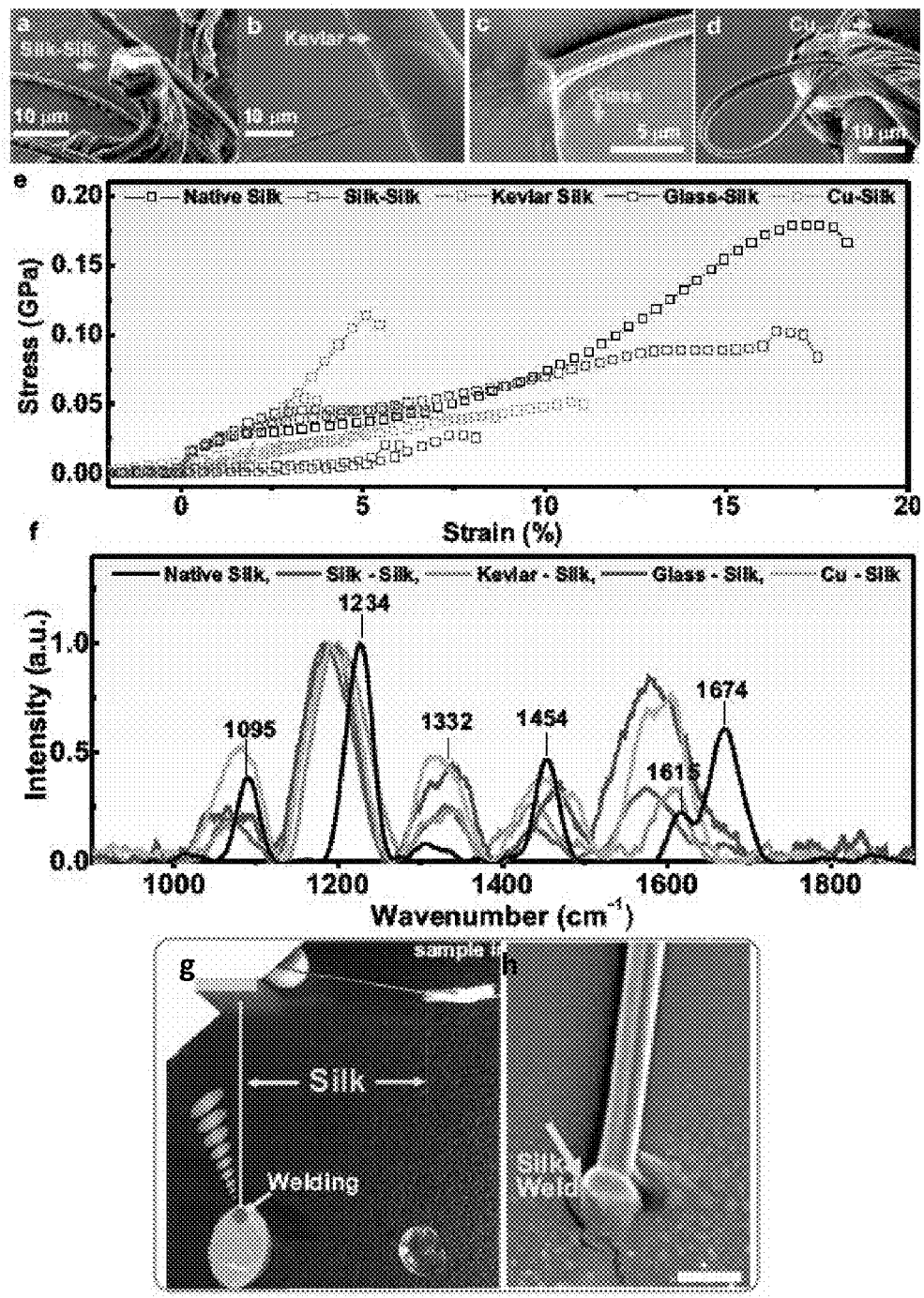
FIG. 6. Fabrication and characterization of micro-welded silk hetero-structures. a-d: Images of welded silk with silk, Kevlar, Cu, and glass. e: The stress-strain curves of silk-silk, silk-Kevlar, silk-Cu and silk-glass joint along with the native silk. The stress is computed by assuming a constant silk diameter. f: Raman spectra accumulated at the welding cite g: Schematic and real image of a contact lens (0:6 gm) suspended from a point welded silk ber h: SEM micrograph of welded silk on PDMS surface FIG. 7. Silk-based functional topological micro-structures. a-c: a micro-spring, coiled-solenoid, and a knotted L-shaped beam, d-e: chiral structures, f: a hemispherical silk particle, g-i: Mobius strips like structures with topological charges. Triangular arrow indicate exposure cite for fs pulses, j: Optical propulsion of silk-rods by a periodic driving using low power green laser in air and in water, h: indicates the displacement of silk structure after the laser irradiation.
Figure 7:
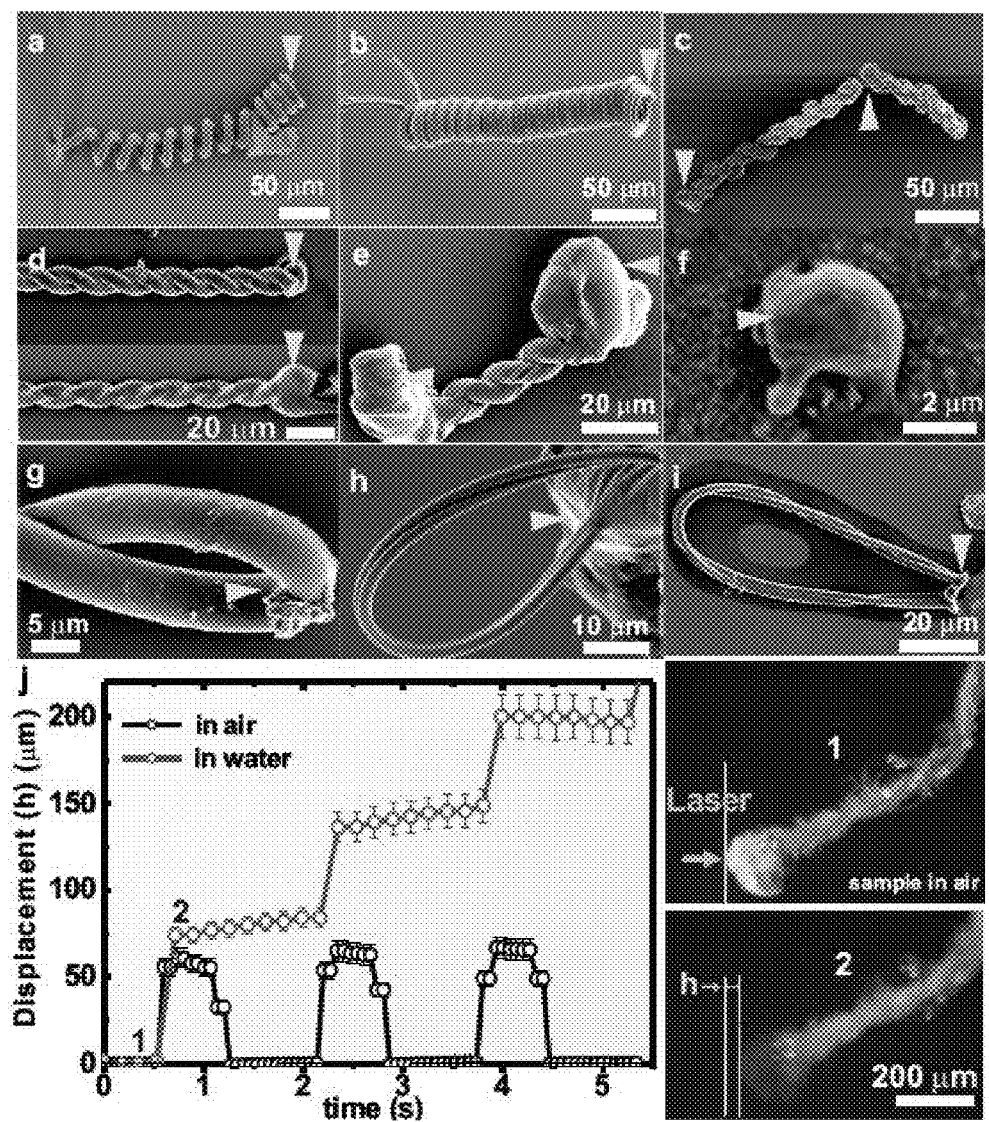

The spider silk was micro-welded to a tissue-like material such as poly-dimethoxysiloxane (PDMS) and contact lens of 9 mm diameter and 600 mg mass Poly (methyl methacrylate) (PMMA) by placing a silk fiber on the edge of fresh (wet) contact lens (FIGS. 6g and 6h). The silk fiber on the lens was exposed to fs pulses such that the damage to contact lens was minimal. This was possible because the contact lens has 500 µm thickness which is much larger compared to the ~3 µm for silk. The weld joint was sufficiently strong to hold the contact lens in air even when it was dried. This suggests that the silk can be used to "glue" tissue-like materials under ambient conditions without using any chemicals or post processing steps.

Advantages

The key advantage of fs pulses is that one can process silk in air with nanoscale precision. Moreover, the key structural building blocks and functionality of silk fibers remain preserved. The present study will have a diverse range of applications. For example, the biocompatibility of silk can be exploited for seamless suturing of silk with other biological tissues including cornea. By welding of silk one can fabricate precision scaffolds for a wide variety of biomedical applications. The optical processing might allow protective silk-coatings on tissues and microscopic structures that can be further explored for delivery of materials inside the cellular organisms. One can also construct bio-compatible materials, silk-based nano-engineering and micro-electro-mechanical systems etc. The present invention takes a definite step towards realizing 3D printed micro structures of silk on various substrates. The optical route to infiltrate silk with nanocomposites (Au, nano-tubes, graphene) could lead to responsive polymers that are sensitive to heat, humidity, magnetic fields or light for various applications. Due to advantages offered by fs pulses, analogous approaches on other biomaterials (shells, keratin, collagen fibers) is also worth exploring.

Example 3

Micro-welding of Silk with Artificial Materials
Methods

Setup and sample preparation: The 2.2 nJ, 7 fs, 85 MHz pulses at 800 nm central wavelength were produced from the Rainbow oscillator (Femtolasers). Two pairs of chirp mirrors compensated the positive dispersion of the triplet lens objective (NA=0.2, working distance 1.7 mm) and delivered the sub-10 fs short pulses at the focus. The 1/e2 focal diameter was about 5 µm.

The dragline silks, diameter 1-6 nm, were extracted from several lab-grown female spiders (*Areneous neoscona*). The 2-5 cm long silk samples were mounted on a 3-axis stage (Thorlabs) with both motorized and piezo-control offering a 25 nm minimum step increment. An electromechanical shutter (2 ms rise-time, Thorlabs) controlled the exposure time. The laser power was attenuated by the ND filter (Optical density-4) and measured with a power meter (Thorlabs). The optical diffraction of the silk was recorded on a white screen.

Optical, Raman and SEM characterization: The UV-Vis-IR absorbance of spider silk and silkworm silk was measured with a spectrometer (Agilent, Cary5000). The confocal imaging of silk was performed using a Leica microscope. The emission spectra were measured with a UV-Vis spectrometer (Thorlabs). The electron microscopy was performed after coating silk with a 20 nm platinum layer. The Raman micro-spectra (Renishaw; 1 µm, spot size) were averaged over 10 scans with λ=633 nm excitation laser at 3 mW power with 2 cm−1 resolution. Tensile strength of the welded joints was measured using a home-made tensile tester with 100 µN force resolution at 0.2 mm/s pulling speed.

Experimental Set-up

A schematic diagram of the experimental set-up is shown in FIG. 1. The few-cycle, nanojoule (nJ) fs pulses were focused through a chirp-mirrors based dispersion compensated triplet lens objective. In order to achieve targeted delivery of fs pulses on the fine silk fiber (0.8-6 µm in diameter), it was mounted on a xyz nano-positioner stage. The silk fiber was roughly positioned at the laser focus by imaging through the dichroic mirror. However, using laser fluence below the damage threshold of silk, the fiber produced a stable diffraction pattern on the screen, which was further used to carefully align the silk in focus with 100 nm precision. The pulse energy was controlled by a neutral density (ND) filter and the exposure time (laser fluence) was varied using a mechanical shutter. The experiment was performed in ambient conditions at 25±1° C. and 50±5% relative humidity.

Photon-induced Bulging and Plasma Ablation

Figure 2:
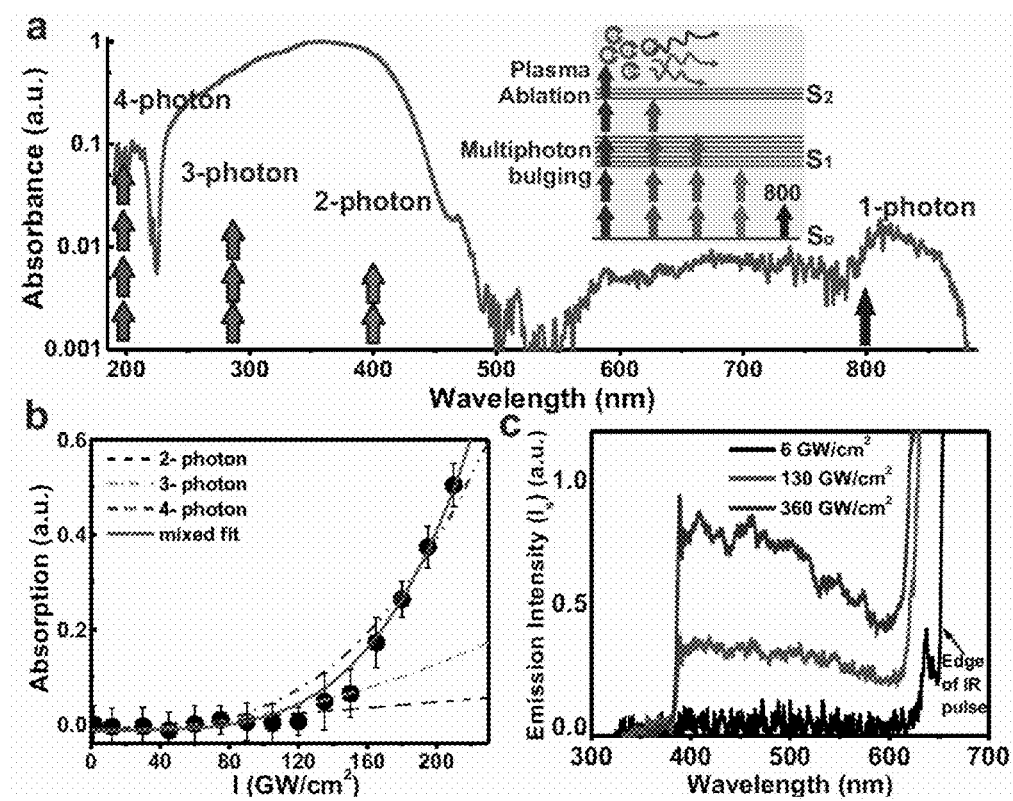
FIG. 2. Mechanisms of laser-silk interaction. a: Absorption spectra of dragline silk in UV-VIS-IR range. b: Absorption of silk as a function of peak intensity (I) of fs pulses. Red line is a mixed fit corresponding to non-linear multiphoton absorption. Dotted lines represent pure 2-, 3-, 4-photon absorption. c: The emission spectra of silk at three different intensities. The cut-off in emission below 380 nm coincides with the maximum of silk absorbance.

The mechanism behind the interaction of sub-10 fs pulses with silk fiber was measured. The UV-Vis-IR linear absorption spectra of the dragline silk (see methods) in the 185-1100 nm wavelength range (FIG. 2a) showed a semi-transparent response around λ=800 nm. However, silk exhibited about 100 times higher absorption at 2, 3, and 4 photon transitions near wavelengths of 400 nm, 266 nm and 200 nm, respectively (vertical arrows in FIG. 2a). The nonlinear absorption coefficients for single silk fiber was measured versus the input laser intensity I (FIG. 2b). The threshold for non-linear absorption was around 80 GW/cm$^2$, which was also the threshold for generation of a broadband emission. The absorption followed a polynomial fit up to 240 GW/cm$^2$. The coefficients for 2, 3, 4 and 5 photon absorptions were $\alpha_2=1\times10^{-2}$ cm/GW, $\alpha_3=2\times10^{-5}$ cm$^3$/GW$^2$, $\alpha_4=4\times10^{-6}$ cm$^5$/GW$^3$, and $\alpha_5=5\times10^{-7}$ cm$^7$/GW$^4$, respectively[36, 37]. The standard Z-scan technique was also used to verify the multiphoton absorption in silk fiber. Previously, a 3-photon absorption process was observed in silk-fibroin solution[37], and enhanced 3- and 4-photon absorption was reported for amyloid fibril solution[36]. Ablation in silk fiber for intensities above 300 GW/cm$^2$ was observed, with an intensified broadband emission at the laser focus (FIG. 2c). This broadband emission was a characteristic signature of laser-induced optical break-down of silk. The peak intensity in our few-cycle pulses was in the 300-1000 GW/cm$^2$ range. A sharp cut-off in the broadband emission below 380 nm was observed which coincided with the maximum light absorption of silk in the UV range, suggesting that simultaneous absorption of multiple photons from the intense fs pulse can effectively excite silk in the UV for ablation. The measured absorbance of silkworm silk was similar to the one for spider silk, suggesting that short fs pulses may induce this type of responses also in silkworm silk. These laser-silk interactions are schematically illustrated in the inset of FIG. 2a, they require high peak powers, and their effect remains localized on the sub-λ scale, well within the focal spot[25, 26].

Figure 3:
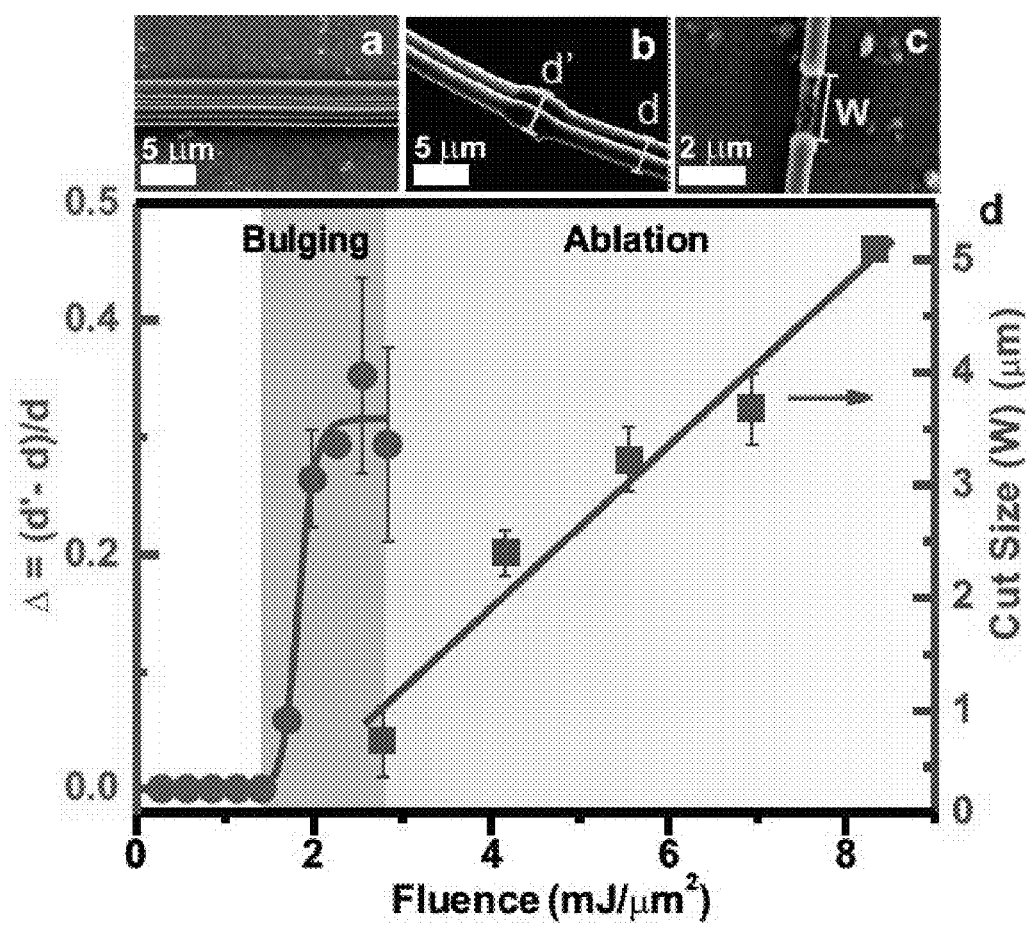
FIG. 3. Bulging and ablation response of the silk as a function of laser fluence. a-c: show SEM images of natural, bulged and ablated silk, respectively. d: shows that bulging regime is characterized by the relative change in silk diameter versus the laser fluence. The ablation regime was quantified by plotting the cut width (W). Error bars indicate average over three measurements.
Figure 4:
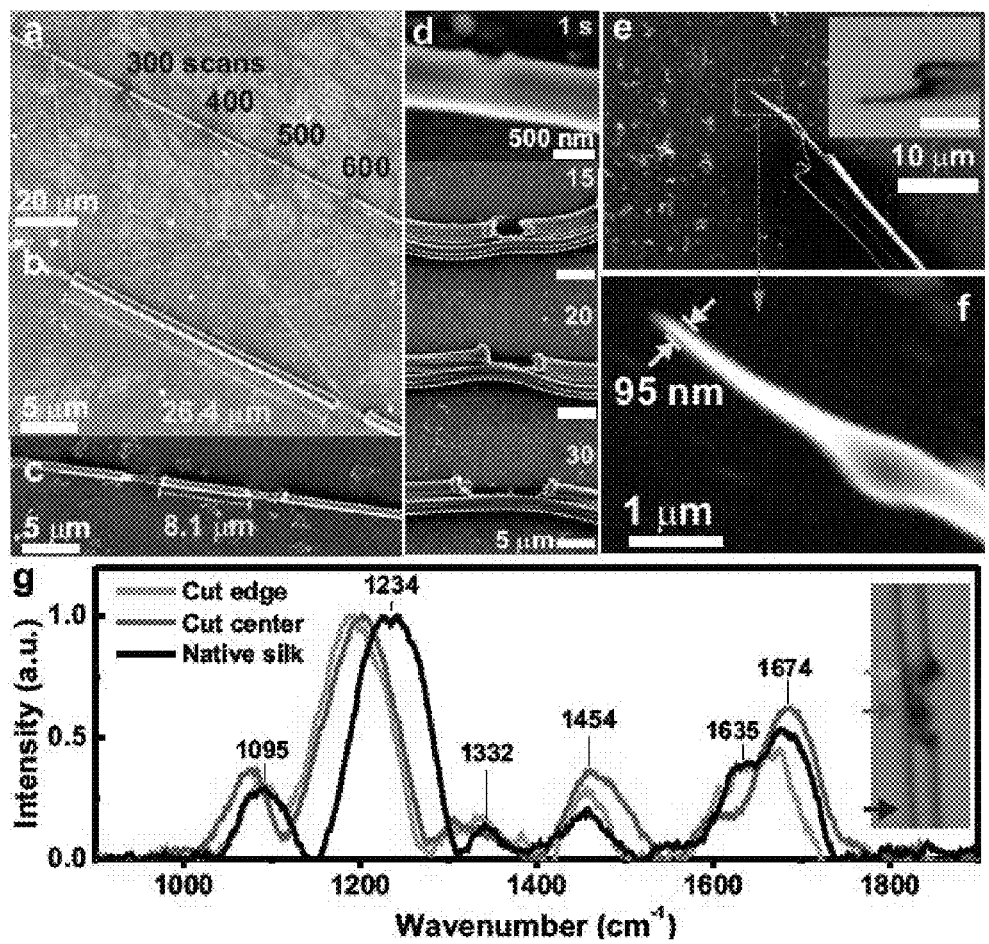
FIG. 4. Non-invasive nano-machining of silk fibers. a-c: Silk rods of 8-26 µm in length, d: nano-grove of width 300 nm to 15 µm. The exposure time of fs pulses is labeled on the picture. e-f: Optical and electron microscope images of a nano-tip fabricated at the end of the fiber. g: Raman spectra of the silk at three different locations near the micro-cut.

The response of dragline silk was further quantified by varying the exposure time for fixed pulse energy. The silk sample (d=1-5 µm) was periodically scanned N times in the focus at 2 mm/s (exposure times 10 ms-100 s) in order to vary the laser fluence on the sample from 0.25 to 9.0 mJ/µm$^2$. It was observed that below a threshold fluence of ~1.25 mJ/µm$^2$, for intensities below 80 GW/cm$^2$, the silk fiber remained unaffected despite the long exposure times. With an increase of the laser fluence, two different regimes, namely photon-induced bulging and plasma-ablation, were observed. For a fluence range of 1.25-3.0 mJ/µm$^2$, the diameter of the silk increased within the focal volume. SEM images of the bulge area showed that the surface was as smooth as in pristine silk. The bulging by measuring fractional change in the silk diameter $\Delta=(d'-d)/d$ was quantified as a function of the laser fluence, where d' and d represent diameters of the bulged and the native silk, respectively. $\Delta$saturated to about 35%, the bulge diameter approaching the size of the focal spot. In the ablation regime (fluence higher than 3.0 mJ/µm$^2$), increasing the fluence gave rise to silk fiber cutting, with sub-100 nm cut steps. In FIG. 3, the cut width W, estimated from SEM images, was plotted which increased linearly with the laser fluence until it reached the focal spot size. In the following, it was demonstrated how these two distinct responses can facilitate minimally invasive controlled processing and microwelding of silk with various materials.

Plasma-assisted Processing

Figure 8:
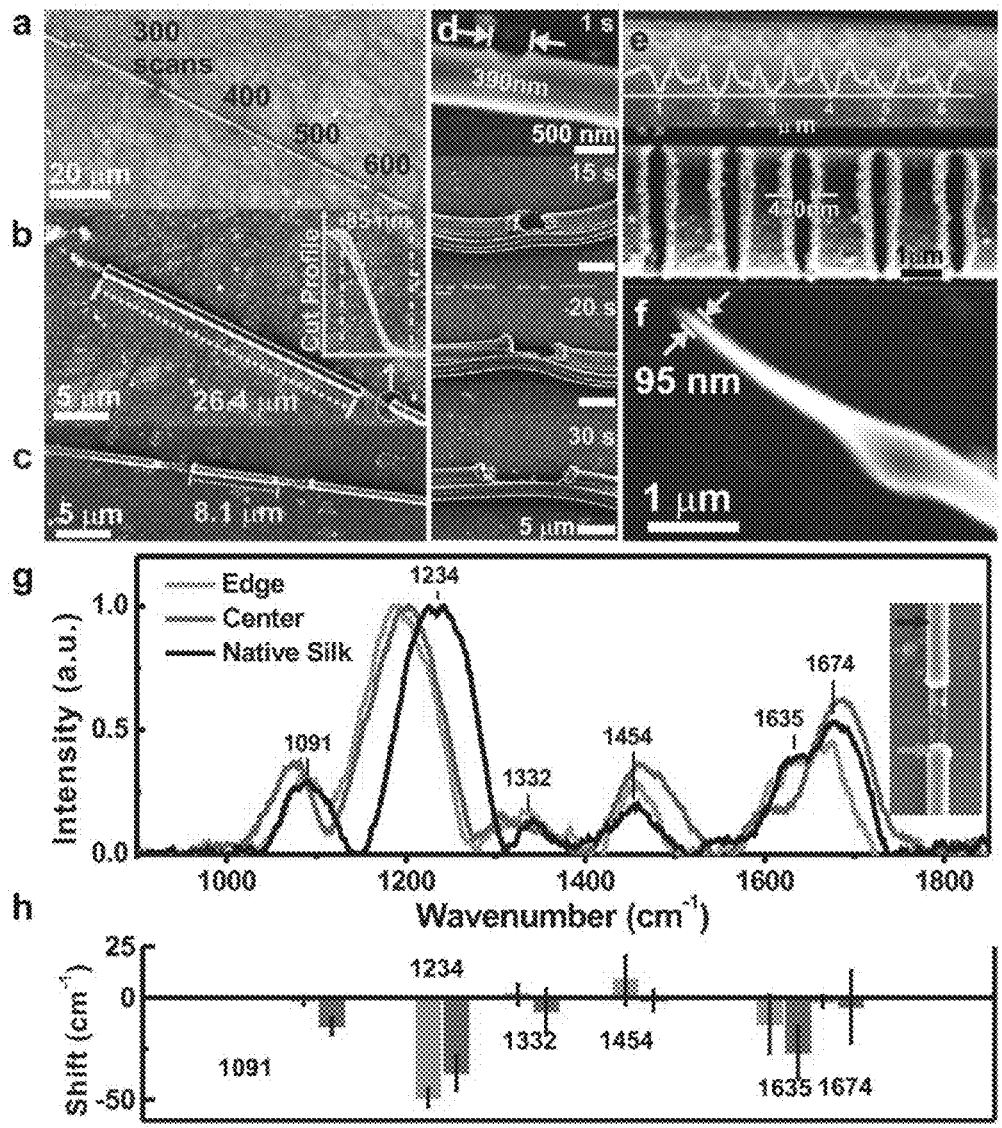
FIG. 8. Localized machining of silk fibers. a-c: Silk-rods, 8-26 μm in length, with cutting precision of 85 nm (inset). d: Nanogroves with controllable widths down to 390 nm. The exposure time is indicated in the images. e: Two examples of periodic grooving with widths of 300 nm (top) and 470 nm (bottom) at 1 μm intervals. f: A nano-tip with 95 nm tip diameter. g: Raman spectra of the silk near the center and the edge of the micro-cut, along with the control. h: Peak shifts for prominent Raman bands. Error bars indicate standard deviation of six Raman spectra, three for control and three for processed samples.

Plasma-ablation allowed diverse non-invasive machining of the silk fiber. One could, for instance, reproducibly dice a roughly 1 µm diameter silk fiber into micro-rods. FIG. 8a-c show SEM micrographs of silk-rods of lengths 8-26 µm. The ends of these micro-rods could be cut with sub-100 nm precision and good surface quality. Using constant peak power above 1000 GW/cm$^2$ and by varying exposure times from 1 to 45 s, localized single or multiple grooves were created with controllable sizes from 390 nm to 10 µm, as shown in FIG. 8d. By scanning fs pulses on silk periodic patterns were made (FIG. 8e) and a silk nano-tip with diameter ~95 nm (FIG. 8f). This demonstrated high precision processing and absence of damage in neighboring regions. The nano-tips, cuts and grooves remained stable in air as well as in vacuum, akin to pristine silk.

In order to confirm that plasma ablation processing did not significantly alter the native molecular structure of the silk, Raman spectra was measured in close vicinity of ablated regions. FIG. 8g shows micro-Raman spectra (in the range of 900-1850 cm$^{-1}$) at center and edge positions of the ablation site, along with the control. Raman shift were computed (FIG. 8h) and band broadening for prominent peaks[27-29] relative to the control samples. Most of the Raman peaks (1091, 1332, 1454, 1674 cm$^{-1}$) were preserved, with negligible Raman shifts and minimal broadening that falls within the error bars. The 1234 cm$^{-1}$ and the side-chain peak at 1605 cm$^{-1}$ undergo a redshift of 30 cm$^{-1}$, which were attribute to the residual bulging of silk by the wings of the Gaussian laser pulse. The preservation of most of the prominent Raman bands during plasma-ablation suggests that sub-10 fs pulses are capable of non-destructive shaping of silk in air.

Photon-induced Bending and Welding

The bulging regime offers a qualitatively different set of processing capabilities. The bulging response was exploited to demonstrate the confined bending of fibers at any angle. FIG. 5a-d show various degrees of bending in air, controlled by varying the laser exposure from 5 to 60 s. The bent fibers were stable in air and vacuum, retained their surface smoothness and showed no evidence of microscopic voids or cracks, as seen by confocal imaging. The tensile strength of bent silk was comparable to native silk.

Figure 5:
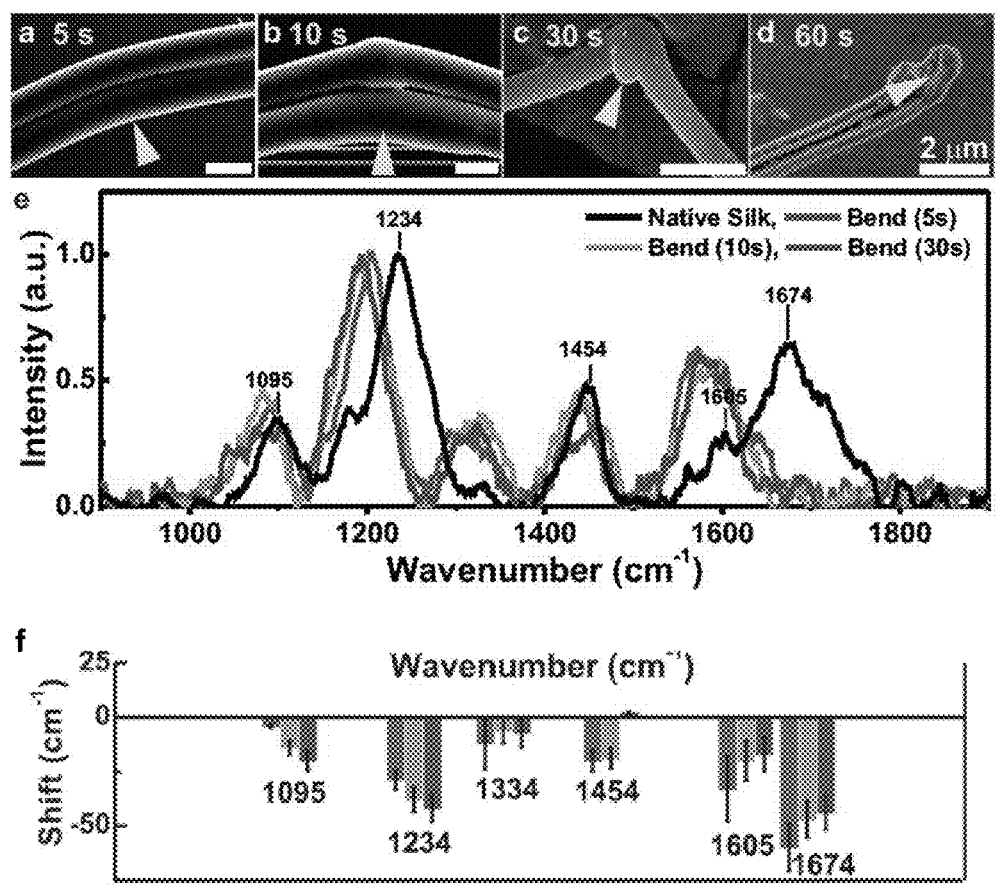
FIG. 5. Confined micro-bending of silk fibers. a-d: Different bend angles are approximately 10°, 30°, 102°, and 180°, respectively. The exposure time of fs pulses is labeled on images. e: Raman micro spectra of silk taken at the bending site along with the native silk. The spectra are normalized to 1234 cm$^{-1}$ peak. f: Peak shift analysis for prominent Raman bands. Error bars indicate standard deviation of six Raman spectra, three for control and three for processed samples.

The micro-Raman spectra at the bending location were also acquired to investigate the resulting molecular deformation in silk (FIGS. 5e, 5f). Analysis revealed that most of the Raman bands show redshifts and positive band broadening. The four Raman bands at 1095 $cm^{-1}$ (assigned to C—C skeleton bond), 1334 $cm^{-1}$ (α-helical conformation), 1454 $cm^{-1}$ (C—H bending mode) and 1605 $cm^{-1}$ (side chains)[28, 29] exhibited small redshifts of ~20±10 $cm^{-1}$. The redshifts in the 1095 $cm^{-1}$ and 1234 $cm^{-1}$ bands increased with increasing bend angle, however, other bands did not show any systematic changes. Similar values of redshifts were reported during tensile and torsional stress and supercontraction of spider silk[8, 27-29]. This indicated that the polypeptide backbone chain remained mostly intact. However, the silk bending caused stress on the protein backbone and side chains, thus changing their bond parameters (bond length, bond angle etc.)[28, 29].

The Raman bands at 1674 $cm^{-1}$ (assigned to polar C=O bonds) and 1234 $cm^{-1}$ (partial C—N double bond) exhibited a larger redshift, ~50±15 $cm^{-1}$. Also, the band at 1334 $cm^{-1}$, assigned to the α-helical conformation in silk[29], was enhanced. This suggested that an increase in the α-helical conformation could be due to rearrangement of weak hydrogen-bonded beta sheets. There could potentially be some chain scission by nonlinear absorption of fs pulses, which results in disruption of some of the beta sheet structures. Furthermore, broadening of some Raman bands indicated enhanced heterogeneity in the bond parameters due to reshaping of the silk fiber[30]. In spite of long exposure to intense sub-10 fs pulses, the key building blocks of the native silk were retained, thus implying resilience of the silk protein.

The bulging regime was successfully utilized for seamless microwelding of two independent silk fibers. Demonstrating this can be used to fabricate all-silk based designer structures. Merging of the contact region of two different silk fibers was demonstrated, when these were exposed to fs pulses for 10-60 s. Optical microscopy (FIG. 9a), confocal microscopy, and SEM images confirmed that the weld regions had no cracks and weld-joints retained surface smoothness. To demonstrate robustness and repeatability of technique silk fibers of various diameters were welded in different configurations.

Silk-based Heterostructures and Applications

The bulging regime facilitates fabrication of precise heterostructures of spider silk by microwelding it with materials like Cu, glass and Kevlar. The micro-welding by fs-pulses remained localized, and avoided damage of the silk and the substrate material. To achieve fine microwelding, the silk fiber was placed in contact with other materials and exposed to the fs pulses (10-60 s exposure time). FIGS. 9a-d show the microwelding of silk with a Kevlar thread (diameter φ=10 μm), a copper wire (φ=100 μm) and a microscope glass slide. These composite structures remained stable both in air and in high vacuum (<$10^{-6}$ Torr).

Figure 9:
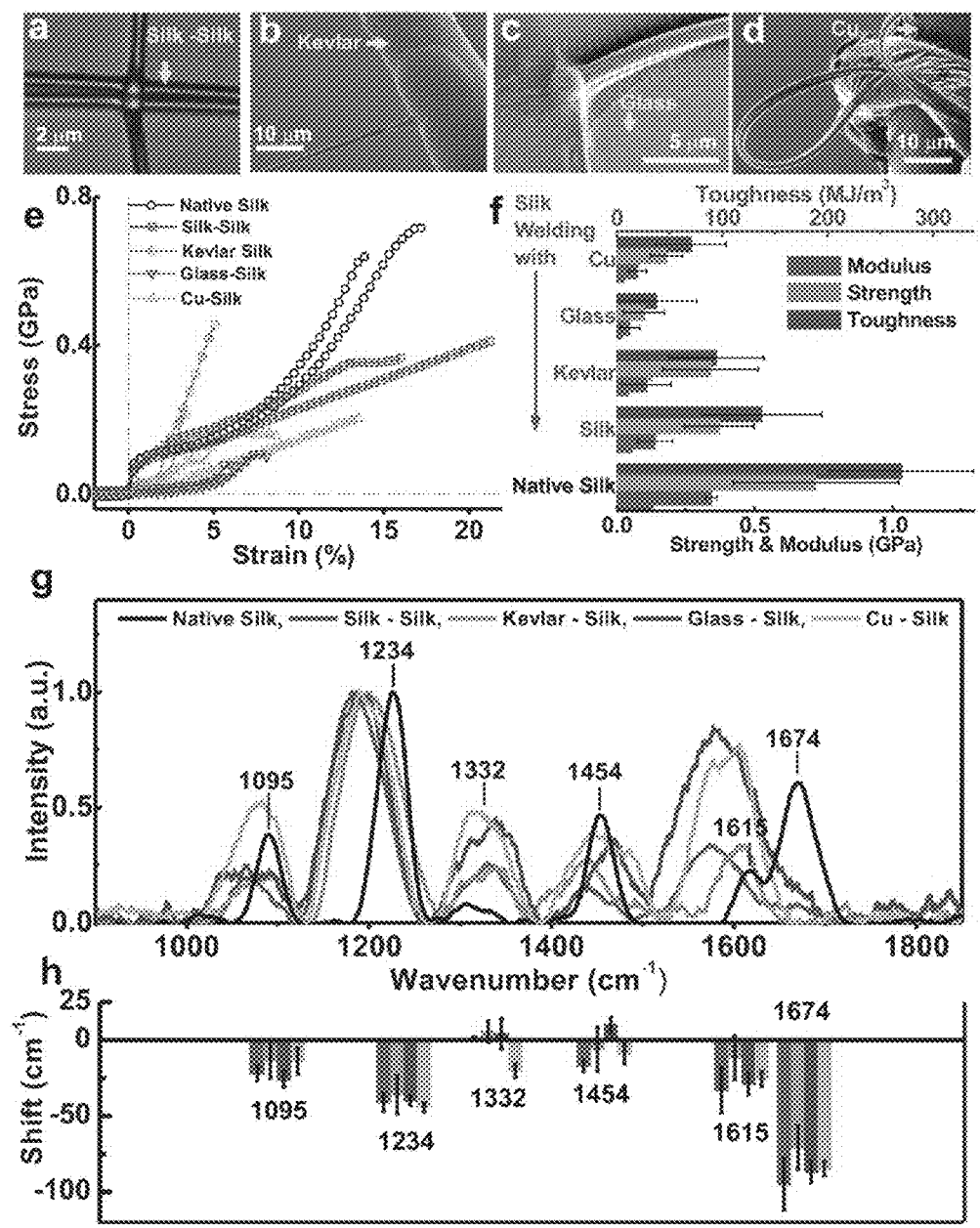
FIG. 9. Fabrication and characterization of microwelded silk heterostructures. a-d: Images of silk welded with silk, Kevlar, Cu, and glass. e: The stress-strain curves of silk-silk, silk-Kevlar, silk-Cu and silk-glass joints, along with native silk. Two independent repeats are shown for each case. The stress was computed by assuming a constant silk diameter. f: Comparison of strength, toughness and Young's modulus for silk heterostructures with the native silk. Error bars indicate standard deviations from five acquisitions for three different samples in each case. g: Raman spectra, and h: corresponding peak shifts for prominent Raman bands at the welding site. Error bars indicate standard deviation of six Raman spectra, three for control and three for processed samples.

The mechanical properties of diverse micro-welded joints were measured. By motorized pulling of the silk end at a constant velocity (0.2 mm/s), the mechanical response of the welded joints was determined. FIG. 9e shows stress-strain curves with two independent repeats for native silk and silk welded with silk, Kevlar, Cu and glass. The values of the Young's modulus were compared, ultimate breaking strength (GPa) and toughness (MJ/$m^3$, area under the curve) in each case (FIG. 9f). The strength of the homogeneous as well as the heterogeneous joints was of the same order of magnitude as the strength of native silk (0.75 GPa)[1-4]. Lower mechanical strength for glass-silk joints could be due to the low bonding affinity between silk and glass.

Micro-Raman analysis was used to understand the molecular scale deformation in silk for all the microwelded joints (FIG. 9g-h). The redshifts and broadening of Raman bands for welded regions exhibited similar features as for the silk-bending, but the magnitude of redshifts in most Raman bands was larger and some Raman bands were broadened. These features indicated higher heterogeneity and disorientation of the side-chains during silk bonding when compared to native silk. The Raman bands corresponding to the polypeptide backbone and side-chains in silk were mostly preserved which suggested that these remained largely intact. The large shift in the 1674 $cm^{-1}$ band together with strengthening of the 1334 $cm^{-1}$ band in silk heterostructures might result from polypeptide chains making van der Waals or hydrogen bonds with the substrate. Preservation of certain molecular bonds of the silk protein also corroborated well with the comparable tensile strength of different microwelded joints.

The proposed optical processing framework was applied to fabricate silk-based micro-structures with various topologies (FIG. 7a-i). For example, by controlled twisting and point welding, a silk-based non-orientable Möbius strip like structure was constructed with different topological charges (1/2, 5/2 and 7/2 turns). Chiral silk structures in the form of left- or right-handed double or multiple strands were also made, which were stabilized by welding their ends. Other topologies that were fabricated from silk fiber included a silk-solenoid, a micro-spring, a silk micro-lens, and knotted bundles (FIG. 10a-h).

The silk structures can find applications, for example, as ultrasensitive force sensors which can detect radiation pressure force. A micro-cantilever (FIG. 10i) made of silk-bundles was welded on a Cu-base. When its free end was exposed to an on-off light cycle, it exhibited a periodic deflection due to the radiation pressure force which was about 100 pN for a continuous-wave (cw) green-laser (0.5-1 W/$mm^2$, FIG. 10j-k). The sensitivity of the silk cantilever can be further enhanced by reducing its spring constant, for example, by lowering the silk diameter. Analogously, a composite silk-Cu microscale device was made to float on the water surface. In response to periodic cw laser irradiation (1 W/$mm^2$), the few mg of Cu-silk heterostructure could be dragged on the water surface (FIG. 10j).

Figure 10:
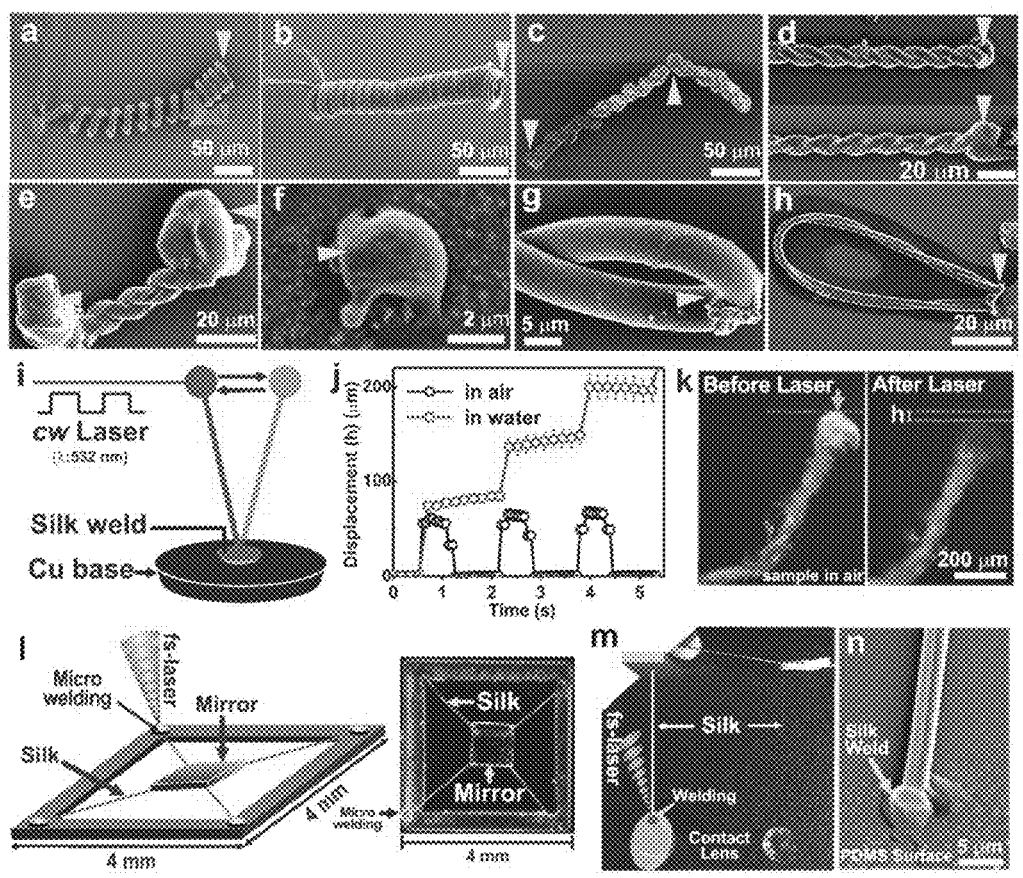
FIG. 10. Functional silk-based topological microstructures. a-c: Micro-spring, coiled-solenoid, and a knotted L-shaped beam. d-e: Chiral structures, f: Silk micro-lens, g-h: Mobiüs strip like structures. Triangular arrows indicate exposure site for fs pulses. i: Schematic of silk cantilever sensor welded on a Cu-base, j: Time-resolved response of the silk cantilever under periodic cw laser exposure (with I~1 W/mm$^2$) in air and of another Silk-Cu device fabricated by welding silk fiber on a base of Cu-wire of 100 μm diameter and 1 mm length on a water surface. k: Image of silk cantilever before and after laser exposure where the yellow lines indicate the displacement from the equilibrium position l: Schematic illustrating fabrication of silk-based trampoline force sensor, and an image of the device. Two identical (3 μm) silk threads were cross-welded on a substrate and a 1 mm$^2$ mirror was welded at the center. m: Schematic and image of a contact lens (0.6 g) suspended from a point-welded silk fiber. n: SEM micrograph of welded silk on a PDMS surface.

A silk-based trampoline sensor was fabricated following a series of welding steps (FIG. 10l). Recently, ultrasensitive trampoline resonators were made using SiN films fabricated using chemical vapor deposition followed by etching techniques[38, 39]. Such optomechanical devices are an attractive alternative to traditional approaches due to the superior mechanical properties, low density and biocompatibility of silk, as well as ease of fabrication under ambient conditions using fs pulses.

Figure 11:
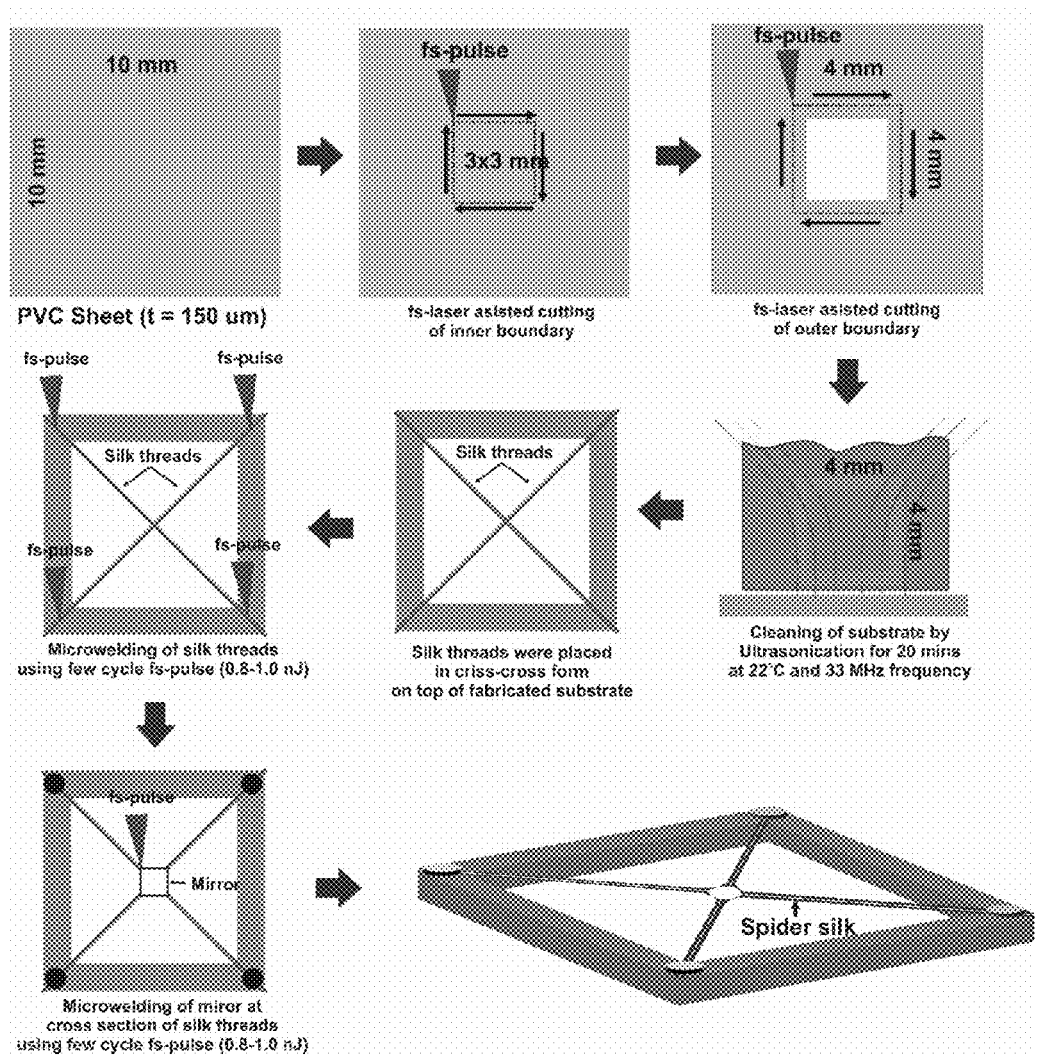
FIG. 11. Non-limiting example of a silk-based trampoline. Schematic illustration of the fabrication of a silk-based trampoline force sensor, and an example of the device.

In another application, the silk was micro-welded with polymeric materials such as PDMS and a wet contact lens (PMMA; FIG. 10m-n). The welded joint was strong enough to support the entire weight of the wet/dry contact lens. This suggests that silk can be used to glue polymeric materials under ambient conditions without any additional chemicals or post-processing steps. FIG. 11 provides a non-limiting example of a silk-based trampoline force sensor. For discussion, please also see Sidhu et al., "The processing and heterostructuring of sild with light" *Nature Materials* Vol. 16 September 2017, which is incorporated herein by reference in its entirety for all intended purposes.

\* \* \*

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

REFERENCES

1. Vollrath, F. & Knight, D. P. Liquid crystalline spinning of spider silk. *Nature* 410, 541-548 (2001).
2. Omenetto, F. G. & Kaplan, D. L. New opportunities for an ancient material. *Science* 329, 528-531 (2010).
3. Vollrath, F. & Porter, D. Spider silk as archetypal protein elastomer. *Soft Matter* 2, 377-385 (2006).
4. Romer, L. & Scheibel, T. The elaborate structure of spider silk: structure and function of a natural high performance fiber. *Prion* 4, 154-161 (2008).
5. Zheng, Y. et al., Directional water collection on wetted spider silk. *Nature* 463, 640-643 (2010).
6. Perrone, G. S. et al., The use of silk-based devices for fracture fixation. *Nat. Commun.* 5, 3385-3394 (2014).
7. Chun, K. Y. et al., Hybrid carbon nanotube yarn artificial muscle inspired by spider dragline silk, *Nat. Commun.* 5, 3322-3331 (2014).
8. Kumar, B. & Singh, K. P. Fatigueless response of spider draglines in cyclic torsion facilitated by reversible molecular deformation. *Appl. Phys. Lett.* 105, 213705 (2014).
9. Lee, S. M. et al., Greatly increased toughness of infiltrated spider silk. *Science* 324, 488-492 (2009).
10. Steven, E. et al., Carbon nanotubes on a spider silk scaffold. *Nat. Commun.* 4, 2435-2443 (2013).
11. Samal, S. K. et al., Biomimetic magnetic silk scaffolds. *ACS Appl. Mater. Interfaces* 7, 6282-6292 (2015).
12. Simmons, A. H., Michal, C. A. & Jelinski, L. W. Molecular orientation and two-component nature of the crystalline fraction of spider dragline silk. *Science* 271, 84-87 (1996).
13. vanBeek, J. D., Hess, S., Vollrath, F. & Meier, B. H. The molecular structure of spider dragline silk: folding and orientation of protein backbone. *PNAS* 99, 10266-10271 (2002).
14. Keten, S. & Buehler, M. J. Atomistic model of the spider silk nanostructure. *Appl. Phys. Lett.* 96, 153701 (2010).
15. Keten, S., Xu, Z., Ihle, B. & Buehler, M. J. Nanoconfinement controls stiffness, strength and mechanical toughness of beta-sheet crystals in silk. *Nat. Mater.* 9, 359-367 (2010).
16. Sponner, A. et al., Composition and hierarchical organization of a spider silk. *PLoS One* 2, e998 (2007).
17. Liu, Y., Shao, Z. & Vollrath, F. Relationships between supercontraction and mechanical properties of spider silk. *Nat. Mater.* 4, 901-905 (2005).
18. Zeplin, P. H. et al., Spider silk coatings as a bioshield to reduce periprosthetic fibrous capsule formation. *Adv. Funct. Mater.* 24, 2658-2666 (2014).
19. Brenckle, M. A. et al., Protein-protein nanoimprinting of silk fibroin films. *Adv. Mater.* 25, 2409-2414 (2013).
20. Cebe, P. et al., Beating the heat—fast scanning melts silk beta-sheet crystals. *Sci. Rep.* 3, 1130 (2013).
21. Applegate, M. B. et al., Laser-based three-dimensional multiscale micropatterning of biocompatible hydrogels for customized tissue engineering scaffolds. *PNAS* 112, 12052-12057 (2015).
22. Moore, A., Koch, M., Mueller, K. & Stuke, M. Precise laser ablation processing of black widow spider silk. *Appl. Phys. A* 77, 353-357 (2003).
23. Gattass, R. R. & Mazur, E. Femtosecond laser micromachining in transparent materials. *Nature Photonics* 2, 219-225 (2008).
24. Tirlapur, U. K. & König, K. Targeted transfection by femtosecond laser. *Nature* 418, 290-291 (2002).
25. Sundaram, S. K. & Mazur, E. Inducing and probing non-thermal transitions in semiconductors using femtosecond laser pulses materials. *Nat. Mater.* 1, 217-224 (2002).
26. Uchugonova, A., König, K., Bueckle, R., Isemann, A. & Tempea, G. Targeted transfection of stem cells with sub-20 femtosecond laser pulses. *Optics Express* 16, 9357-9364 (2008).
27. Lefèvre, T., Mercier, F. P., Dubé, J.-F. R. & Pézolet, M. Structure of silk by Raman spectromicroscopy: from spinning glands to the fiber. *Biopolymers* 97, 322-336 (2011).
28. Sirichaisit, J., Young, R. J. & Vollrath, F. Molecular deformation in spider dragline silk subjected to stress. *Polymer* 41, 1223-1227 (2000).
29. Shao, Z., Vollrath, F., Sirichaisit, J. & Young, R. J. Analysis of spider silk in native and supercontracted state using Raman spectroscopy. *Polymer* 40, 2493-2500 (1999).
30. Kitagawa, T., Yabukia, K. & Young, R. J. An investigation into the relationship between processing, structure and properties for high-modulus PBO fibres. Part 1. Raman band shifts and broadening in tension and compression. *Polymer* 42, 2101-2112 (2001).
31. Porter, D. & Vollrath, F. Silk as a biomimetic ideal for structural polymers. *Adv. Mater.* 21, 487-492 (2009).
32. Altman, D. G. et al., Silk-based biomaterials. *Biomaterials* 24, 401-416 (2003).
33. Qin, Z. et al., Structural optimization of 3D-printed synthetic spider webs for high strength. *Nat. Commun.* 6, 7038-7045 (2015).
34. Buehler, M. J. & Yung, Y. C. Deformation and failure of protein materials in physiologically extreme conditions and disease. *Nat. Mater.* 8, 175-188 (2009).
35. Cohen Stuart, M. A. et al., Emerging applications of stimuli-responsive polymer materials. *Nat. Mater.* 9, 101-113 (2010).
36. Hanczyc, P., Samoc, M. & Norden B. Multiphoton absorption in amyloid protein fibres. *Nature Photonics* 7, 969-972 (2013).
37. Applegate, M. B., Marelli, B., Kaplan, D. L. & Omenetto, F. G. Determination of multiphoton absorption of silk fibroin using the Z-scan technique. *Optics Express* 21, 29637-29642 (2013).
38. Norte, R. A., Moura, J. P, & Gröblacher, S. Mechanical resonators for quantum optomechanics experiments at room temperature. *Phys. Rev. Lett.* 116, 147202 (2016).

39. Reinhardt, C., Müller, C., Bourassa, A., & Sankey, J. C. Ultralow-noise SiN trampoline resonators for sensing and optomechanics. *Phys. Rev. X* 6, 021001 (2016).

We claim:

1. A non-invasive method for Nano processing of silk comprising:
   a) quantifying non-linear multiphoton response of a silk material as a function of laser fluence induced by a pulsed femtosecond laser beam of predetermined laser characteristics; and
   b) micro structuring or heterostructuring of silk material upon exposure of the femtosecond laser beam.

2. The method of claim 1, wherein in step a) quantifying non-linear multiphoton response of the silk material comprises:
   a) focusing the femtosecond laser beam at a focal point under ambient conditions;
   b) exposing a portion of the silk material at said focal point;
   c) raster scanning the portion of the silk material in the focus;
   d) displaying real time image of said exposed portion of the silk material; and
   e) determining a change in a physical dimension of said portion of the silk material by varying the laser fluence at the portion of the silk material.

3. The method of claim 2, wherein in step e) determining a change in physical dimension of said portion of silk material by varying the laser fluence comprises:
   a) determining an effect of a bulging at the portion of the silk material for a laser fluence range between 1.25 to 3.0 mJ/$\mu m^2$; and
   b) determining an effect of a plasma ablation at the portion of the silk material for a laser fluence range between 3.0 mJ/$um^2$ to 9 mJ/$\mu m^2$
      wherein the bulging and the plasma ablation defines a change in physical dimension of the silk material without causing any collateral damage onto the material, said effects of bulging and plasma ablation being based on non-linear multiphoton absorption response of the silk material to the pulsed femtosecond laser beam.

4. The method of claim 2, wherein in step b) exposing the portion of silk material at said focal point comprises:
   a) focusing the femto-second (fs) laser pulses through a chirp mirror based dispersion compensated triplet lens objective;
   b) aligning the silk sample in the laser focus by imaging through a dichroic mirror;
   c) aligning the silk sample in the laser focus by diffraction imaging in transmission.

5. The method of claim 2, wherein the ambient conditions for performing said method include a temperature between 24°-26° C. in air and a relative humidity between 45% to 55%.

6. The method of claim 2, wherein the step of exposing comprises exposing the portion of the silk material by varying an exposure time within a range of 10 ms to 100 s; wherein the step of raster scanning comprises periodically scanning the portion of the silk material at a scan rate of 2 mm/s; and wherein the step of varying the laser fluence comprises varying the laser fluence within a range of 0.25 to 9.0 mJ/$\mu m^2$.

7. The method of claim 1, wherein in step b) micro structuring comprises preparation of topological microstructures including micro-springs, coiled solenoid, mobius strips, chiral helices, or knots.

8. The method of claim 1, wherein step b) heterostructuring comprises seamless welding of the silk material with an artificial or biological material.

9. The method of claim 8, wherein seamless welding of silk material comprises:
   a) contacting the silk material with the artificial or biological material; and
   b) focusing the femtosecond laser beam to the site of contact resulting in fabrication of a micro welded structure by operating the laser beam at bulging regime.

10. The method of claim 9, wherein the femtosecond laser beam used for micro-welding has energy between 0.8-1.0 nJ and an exposure time between 30-60 s having a scan rate of 2 mm/s.

11. A system for quantifying optical response of a silk material, the system comprising:
    a focusing unit for focusing a pulsed femtosecond laser beam of predetermined laser characteristics at a focal point;
    a three dimensionally movable translation stage support for holding the silk material and exposing a portion of said silk material at said focal point;
    displaying unit for displaying real time image of focused portion of the silk material.

12. The system of claim 11, wherein determining change in physical dimension of the portion of silk material by varying the laser fluence, comprises:
    a) determining an effect of a bulging at the portion of the silk material for a laser fluence range between 1.25 to 3.0 mJ/$\mu m2$; and
    b) determining an effect of a plasma ablation at the portion of the silk material for a laser fluence range between 3.0 mJ/$um^2$ to 9 mJ/$\mu m^2$,
       wherein the bulging and the plasma ablation defines a change in physical dimension of the silk material without causing any collateral damage onto the material, said effects of bulging and plasma ablation are determined by exploiting the non-linear multiphoton absorption response of the pulsed femtosecond laser beam towards the silk material.

13. A method for preparation of a silk based nanosensor comprising:
    a) cleaning a substrate base using ultrasonication;
    b) placing the silk thread over the substrate and microwelding one or more silk threads onto the substrate, wherein silk threads comprise the nanostructured or heterostructured silk fibers; and wherein nano structuring or heterostructuring involves the steps of (i.) quantifying non-linear multiphoton response of a silk material as a function of laser fluence induced by a pulsed femtosecond laser beam of predetermined laser characteristics; and (ii.) micro structuring or heterostructuring of silk material upon exposure of the femtosecond laser beam; and
    c) obtaining the fabricated biosensor and propelling the same in air or a fluid.

14. The method of claim 13 for the preparation of a cantilever nanosensor, wherein the method comprises:
    a) cleaning the substrate using Methanol: Acetone solution and ultra-sonicating for a suitable time period;
    b) extracting and braiding two threads of spider silk dragline;
    c) fusing or welding the end of threads fs-pulses;
    d) exposing the threads to the pulses;
    e) welding one end of the thread with substrate;

f) bending the other fused end at a certain angle as a function of exposure time and energy; and g) obtaining the silk cantilever nanosensor.

15. The method of claim 14 for the preparation of a cantilever nanosensor, wherein the method comprises:
   a) cleaning the substrate using 3:1 (Methanol:Acetone) solution and ultra-sonicating for 30 min;
   b) extracting and braiding two threads of spider silk dragline of 1-3 µm;
   c) fusing or welding the end of threads with nanojoule fs-pulses;
   d) exposing the threads to the pulses 100 times at the speed of 2 mm/s with the pulsed average energy between 0.8-1 nJ;
   e) welding one end of the thread with substrate with an exposure time of about 30 s and energy between 0.8-1.0 nJ;
   f) bending the other fused end at an angle between 45-60° as a function of exposure time (0.3-5 s) and energy between 0.8-1.0 nJ; and
   g) obtaining the silk cantilever nanosensor.

16. A cantilever nanosensor as obtained by the process claimed in claim 14.

17. A method for testing the sensitivity of the nanosensors as claimed in claim 16, comprising propelling the nanosensor in air or a fluid medium and checking its responsiveness to pressure, force, light, or other external factor.

18. The method of claim 13 for the preparation of a trampoline nanosensor, wherein the method comprises:
   a) fabricating the substrate by cutting a PVC sheet by automated scan of femtosecond laser pulses with certain incident energy and a repetition rate, followed by sifting;
   b) cleaning the substrate using ultrasonication for suitable time at room temperature;
   c) placing the substrate on a glass slide and then placing the spider silk fibers over in a criss-cross manner;
   d) exposing the four corners of the fabricated substrate with Fs-laser pulses for micro-welding of silk on PVC substrate;
   e) placing a mirror at the center of criss-crossed silk threads and microwelding it with aforementioned parameters; and
   f) obtaining the fabricated trampoline sensor.

19. The method of claim 18 for the preparation of a trampoline nanosensor, wherein the method comprises:
   a) fabricating the substrate by cutting a PVC sheet of about 150 µm thickness (outer parameters of about 4×4 mm2a and inner square area of about 3×3 mm2) by automated scan of femtosecond laser pulses with an incident energy of about 50 µJ and a repetition rate of 50 repetitions with a scan rate of 2 mm/s. Z-axis (focal plane), sifting with a step of 30 µm per repetition;
   b) cleaning the substrate using ultrasonication for about 20 min at room temperature;
   c) placing the substrate on a glass slide and then placing the spider silk fibers over in a criss-cross manner;
   d) exposing the four corners of the fabricated substrate with Fs-laser pulses for micro-welding of silk on PVC substrate with following parameters: Laser energy: 0.8-1 nJ, exposure time between 30-60 s at the scan rate of 2 mm/s;
   e) placing a mirror at the center of criss-crossed silk threads and microwelding it with aforementioned parameters; and
   f) obtaining the fabricated trampoline sensor.

20. A trampoline nanosensor as obtained by the process claimed in claim 18.

* * * * *